United States Patent
Heck et al.

(10) Patent No.: US 7,838,654 B2
(45) Date of Patent: *Nov. 23, 2010

(54) TUBULIN REGULATORY ELEMENTS FOR USE IN PLANTS

(76) Inventors: Gregory R. Heck, 2200 Divot Dr., Crystal Lake Park, MO (US) 63131; Marianne Malven, 130 Irene Dr., Ellisville, MO (US) 63011; James D. Masucci, 4 Foxcliff Ct., Ballwin, MO (US) 63011; Jinsong You, 1685 Carman Mill Dr., Manchester, MO (US) 63021

( * ) Notice: Subject to any disclaimer, the term of this patent is extended or adjusted under 35 U.S.C. 154(b) by 0 days.

This patent is subject to a terminal disclaimer.

(21) Appl. No.: 12/389,314

(22) Filed: Feb. 19, 2009

(65) Prior Publication Data

US 2009/0186765 A1 Jul. 23, 2009

Related U.S. Application Data

(62) Division of application No. 10/925,392, filed on Aug. 25, 2004, now Pat. No. 7,511,130.

(60) Provisional application No. 60/497,523, filed on Aug. 25, 2003.

(51) Int. Cl.
C07H 21/04 (2006.01)
C12N 15/82 (2006.01)
A01H 5/00 (2006.01)

(52) U.S. Cl. ............... 536/24.1; 536/23.2; 800/278; 800/295; 800/298; 800/300; 435/468; 435/419

(58) Field of Classification Search .............. None
See application file for complete search history.

(56) References Cited

U.S. PATENT DOCUMENTS

| | | | |
|---|---|---|---|
| 5,530,196 A | 6/1996 | Fraley et al. | 800/298 |
| 5,635,618 A * | 6/1997 | Capellades et al. | 800/288 |
| 5,641,876 A | 6/1997 | McElroy et al. | 536/24.1 |
| 6,040,497 A | 3/2000 | Spencer et al. | 800/288 |
| 6,051,753 A | 4/2000 | Comai et al. | 800/278 |
| 6,177,611 B1 | 1/2001 | Rice | 800/278 |
| 6,906,245 B1 | 6/2005 | Nakajima et al. | 800/300 |
| 7,511,130 B2 * | 3/2009 | Heck et al. | 536/24.1 |

FOREIGN PATENT DOCUMENTS

| | | |
|---|---|---|
| EP | 0 652 286 | 5/1995 |
| WO | WO 95/06128 | 3/1995 |

OTHER PUBLICATIONS

Breviario, D. *Oryza sativa* (indica cultivar-group) partial tubA2 gene for tubulin alpha, exons 1-2 and promoter. (2002) GenBank Accession AJ488062; pp. 1-3.*
Cho Regulation of root hair initiation and expansin gene expression in *Arabidopsis*, The Plant Cell, 14:3237-3253, 2002.
Donald et al., "Mutation of either G box or I box sequences profoundly affects expression from the a*Aabidopsis* rbcS-1A promoter," *EMBO J.*, 9:1717-1726, 1990.
EMBL Database, Accession No. AC137924, Dec. 11, 2002.
EMBL Database, Accession No. AJ488063, Nov. 22, 2002.
Fiume et al., "Introns are key regulatory elements of rice tubulin expression," *Planta*, 218:693-703, 2004.
GenBank Accession No. AJ488063, Nov. 22, 2002.
Jeon et al., "Tissue-preferential expression of a rice α-tubulin gene, OsTubA1, mediated by the first intron," *Plant Physiology*, 123:1005-1014, 2000.
Kim et al., "A 20 nucleotide upstream element is essential for the nopaline synthase (nos) promoter activity," *PMB*, 24:105-117, 1994.
Maiti et al., "Promoter/leader deletion analysis and plant expression vectors with the figwort mosaic virus (FMV) full length transcript (FLt) promoter containing single or double enhancer domains," *Transgenic Research*, 6:143-156, 1997.
Piechulla et al., "Identification of tomato Lhc promoter regions necessary for circadian expression," *Plant Mol. Biol.*, 38:655-662, 1998.
Qin et al., "Molecular cloning of three rice α-tubulin isotypes: differential expression in tissues and during flower development," *Biochimica et Biophysica Acta*, 1354:19-23, 1997.
Welsch et al., "Structural and functional characterization of the phytoene synthase promoter from *Arabidopsis thaliana*," *Planta*, 216:523-534, 2003.

* cited by examiner

*Primary Examiner*—Cathy Kingdon Worley
(74) *Attorney, Agent, or Firm*—Erin C. Robert, Esq.; SNR Denton US LLP

(57) ABSTRACT

The present invention provides polynucleotide molecules isolated from *Zea mays* and *Oryza sativa* and useful for expressing transgenes in plants. The present invention also provides expression constructs containing the polynucleotide molecules useful for expressing transgenes in plants. The present invention also provides transgenic plants and seeds containing the polynucleotide molecules useful for expressing transgenes in plants.

18 Claims, 2 Drawing Sheets

SEQUENCE LISTING

<160> NUMBER OF SEQ ID NOS: 11

<210> SEQ ID NO 1
<211> LENGTH: 2190
<212> TYPE: DNA
<213> ORGANISM: Oryza sativa

<400> SEQUENCE: 1

```
gcctcgagac aacaacatgc ttctcatcaa catggaggga agagggaggg agaaagtgtc      60
gcctggtcac ctccattgtc acactagcca ctggccagct ctcccacacc accaatgcca     120
ggggcgagct ttagcacagc caccgcttca cctccaccac cgcactaccc tagcttcgcc     180
caacagccac cgtcaacgcc tcctctccgt caacataaga gagagagaga agaggagagt     240
agccatgtgg ggaggaggaa tagtacatgg ggcctaccgt ttggcaagtt attttgggtt     300
gccaagttag gccaataagg ggagggattt ggccatccgt ttggaaaggt tattggggta     360
gtatcttttt actagaattg tcaaaaaaaa atagtttgag agccatttgg agaggatgtt     420
gcctgttaga ggtgctctta ggacatcaaa ttccataaaa acatcagaaa aattctctcg     480
atgaagattt ataaccacta aaactgccct caattcgaag ggagttcaaa acaattaaaa     540
tcatgttcga attgagtttc aatttcactt taacccttt gaaatctcaa tggtaaaaca      600
tcaacccgtc aggtagcatg gttcttttta ttcctttcaa aaagagttaa ttacaaacag     660
aatcaaaact aacagttagg cccaaggccc atccgagcaa acaatagatc atgggccagg     720
cctgccacca ccctccccct cctggctccc gctcttgaat ttcaaaatcc aaaaatatcg     780
gcacgactgg ccgccgacgg agcgggcgga aaatgacgag acaaccccctc gaattctacc     840
ccaactacgc ccaccaaccc acacgccact gacaatccgg tcccacccttt gtgggcccac     900
ctacaagcga gacgtcagtc gctcgcagca accagtgggc ccacctccca gtgagcggcg     960
ggtagatctg gactcttacc cacccacact aaacaaaacg gcatgaatat tttgcactaa    1020
aaccctcaga aaaattccga tattccaaac cagtacagtt cctgaccgtt ggaggagcca    1080
aagtggagcg gagtgtaaaa ttgggaaact taatcgaggg ggttaaacgc aaaaacgccg    1140
aggcgcctcc cgctctatag aaaggggagg agtgggaggt ggaaaccctta ccacaccgca    1200
gagaaaggcg tcttcgtact cgcctctctc cgcgccctcc tccgccgccg ctcgccgccg    1260
ttcgtctccg ccgccaccgg ctagccatcc aggtaaaaca aacaaaaacg gatctgatgc    1320
ttccattcct ccgtttctcg tagtagcgcg cttcgatctg tgggtggatc tgggtgatcc    1380
```

```
tggggtgtgg ttcgttctgt ttgatagatc tgtcggtgga tctggccttc tgtggttgtc    1440
gatgtccgga tctgcgtttt gatcagtggt agttcgtgga tctggcgaaa tgttttggat    1500
ctggcagtga gacgctaaga atcgggaaat gatgcaatat taggggggtt tcggatgggg    1560
atccactgaa ttagtctgtc tccctgctga taatctgttc cttttttggta gatctggtta   1620 gtgtatgttt gtttcggata gatctgatca atgcttgttt gttttttcaa attttctacc    1680
taggttgtat aggaatggca tgcggatctg gttggattgc catgatccgt gctgaaatgc    1740
ccctttggtt gatggatctt gatattttac tgctgttcac ctagatttgt actcccgttt    1800
atacttaatt tgttgcttat tatgaataga tctgtaactt aggcacatgt atggacggag    1860
tatgtggatc tgtagtatgt acattgctgc gagctaagaa ctatttcaga gcaagcacag    1920
aaaaaaatat ttagacagat tgggcaacta tttgatggtc tttggtatca tgctttgtag    1980
tgctcgtttc tgcgtagtaa tcttttgatc tgatctgaag ataggtgcta ttatattctt    2040
aaaggtcatt agaacgctat ctgaaaggct gtattatgtg gattggttca cctgtgactc    2100
cctgttcgtc ttgtcttgat aaatcctgtg ataaaaaaaa ttcttaaggc gtaatttgtt    2160
gaaatcttgt tttgtcctat gcagcctgat                                     2190

<210> SEQ ID NO 2
<211> LENGTH: 1206
<212> TYPE: DNA
<213> ORGANISM: Oryza sativa

<400> SEQUENCE: 2
gcctcgagac aacaacatgc ttctcatcaa catggaggga agagggaggg agaaagtgtc      60
gcctggtcac ctccattgtc acactagcca ctggccagct ctcccacacc accaatgcca     120
ggggcgagct ttagcacagc caccgcttca cctccaccac cgcactaccc tagcttcgcc     180
caacagccac cgtcaacgcc tcctctccgt caacataaga gagagagaga agaggagagt     240
agccatgtgg ggaggaggaa tagtacatgg ggcctaccgt ttggcaagtt attttgggtt     300
gccaagttag gccaataagg ggagggattt ggccatccgg ttggaaaggt tattggggta     360
gtatcttttt actagaattg tcaaaaaaaa atagtttgag agccatttgg agaggatgtt     420
gcctgttaga ggtgctctta ggacatcaaa ttccataaaa acatcagaaa aattctctcg     480
atgaagattt ataaccacta aaactgccct caattcgaag ggagttcaaa acaattaaaa     540
tcatgttcga attgagtttc aatttcactt taacccettt gaaatctcaa tggtaaaaca     600
tcaacccgtc aggtagcatg gttcttttta ttcctttcaa aaagagttaa ttacaaacag     660
aatcaaaact aacagttagg cccaaggccc atccgagcaa acaatagatc atgggccagg     720
cctgccacca ccctccccct cctggctccc gctcttgaat ttcaaaatcc aaaaatatcg     780
gcacgactgg ccgccgacgg agcgggcgga aaatgacgga acaacccctc gaattctacc     840
ccaactacgc ccaccaaccc acacgccact gacaatccgg tcccacccct gtgggcccac     900
ctacaagcga gacgtcagtc gctcgcagca accagtgggc ccacctccca gtgagcggcg     960
ggtagatctg gactcttacc cacccacact aaacaaaacg gcatgaatat tttgcactaa    1020
aaccctcaga aaaattccga tattccaaac cagtacagtt cctgaccgtt ggaggagcca    1080
aagtggagcg gagtgtaaaa ttgggaaact taatcgaggg ggttaaacgc aaaaacgccg    1140
aggcgcctcc cgctctatag aaagggggagg agtgggaggt ggaaacccta ccacaccgca    1200
gagaaa                                                               1206
```

<210> SEQ ID NO 3
<211> LENGTH: 582
<212> TYPE: DNA
<213> ORGANISM: Oryza sativa

<400> SEQUENCE: 3
cagggttctt gcctggtgcc ttggcaatgc ttgattactg ctgctatcct atgatctgtc    60
cgtgtgggct tctatctatc agtttgtgtg tctggttttg aaaaacattt gcttttcgat   120
tatgtagggt ttgcttgtag ctttcgctgc tgtgacctgt gttgtttatg tgaaccttct   180
ttgtggcatc tttaatatcc aagttcgtgg tttgtcgtaa acgaagcct ctacttcgta    240
aagttgtgtc tatagcattg aaatcgtttt tttgctcgag ataattgtg acctttagtt    300
ggcgtgaaac tagttttgga tatctgattc tctggttcgc aatcttgaga tcgtcgctgc   360
ttaggtgagc taagtgatgt tcctaagtaa atgctcctca ccagaatacg tagctgtgtg   420
aaaagagaac gcgtgaatac gtagctgtgt aaagattgtg tcccaagtaa acctcagtga   480
ttttttgtttg gatttttaat ttagaaacat tcgactggga gcggctagag ccacacccaa  540
gttcctaact atgataaagt tgctctgtaa cagaaaacac ca                     582

<210> SEQ ID NO 4
<211> LENGTH: 892
<212> TYPE: DNA
<213> ORGANISM: Oryza sativa

<400> SEQUENCE: 4 gtaaacaaa caaaaacgga tctgatgctt ccattcctcc gtttctcgta gtagcgcgct     60
tcgatctgtg ggtggatctg ggtgatcctg gggtgtggtt cgttctgttt gatagatctg   120
tcggtggatc tggccttctg tggttgtcga tgtccggatc tgcgttttga tcagtggtag   180
ttcgtggatc tggcgaaatg ttttggatct ggcagtgaga cgctaagaat cgggaaatga   240
tgcaatatta ggggggtttc ggatggggat ccactgaatt agtctgtctc cctgctgata   300
atctgttcct ttttggtaga tctggttagt gtatgtttgt ttcggataga tctgatcaat   360
gcttgtttgt tttttcaaat tttctaccta ggttgtatag gaatggcatg cggatctggt   420
tggattgcca tgatccgtgc tgaaatgccc ctttggttga tggatcttga tattttactg   480
ctgttcacct agatttgtac tcccgtttat acttaatttg ttgcttatta tgaatagatc   540
tgtaacttag gcacatgtat ggacggagta tgtggatctg tagtatgtac attgctgcga   600
gctaagaact atttcagagc aagcacagaa aaaatatttt agacagattg ggcaactatt   660
tgatggtctt tggtatcatg ctttgtagtg ctcgtttctg cgtagtaatc ttttgatctg   720
atctgaagat aggtgctatt atattcttaa aggtcattag aacgctatct gaaaggctgt   780
attatgtgga ttggttcacc tgtgactccc tgttcgtctt gtcttgataa atcctgtgat   840
aaaaaaaatt cttaaggcgt aatttgttga aatcttgttt tgtcctatgc ag          892

<210> SEQ ID NO 5
<211> LENGTH: 86
<212> TYPE: DNA
<213> ORGANISM: Oryza sativa

<400> SEQUENCE: 5
ggcgtcttcg tactcgcctc tctccgcgcc ctcctccgcc gccgctcgcc gccgttcgtc    60
tccgccgcca ccggctagcc atccag                                       86

```
<210> SEQ ID NO 6
<211> LENGTH: 32
<212> TYPE: DNA
<213> ORGANISM: Artificial Sequence
<220> FEATURE:
<223> OTHER INFORMATION: Synthetic oligonucleotide primer

<400> SEQUENCE: 6
gacaagcttg cctcgagaca acaacatgct tc                               32

<210> SEQ ID NO 7
<211> LENGTH: 38
<212> TYPE: DNA
<213> ORGANISM: Artificial Sequence
<220> FEATURE:
<223> OTHER INFORMATION: Synthetic oligonucleotide primer

<400> SEQUENCE: 7
attccatggc ggctagccgg tggcggcgga gacgaacg                         38

<210> SEQ ID NO 8
<211> LENGTH: 39
<212> TYPE: DNA
<213> ORGANISM: Artificial Sequence
<220> FEATURE:
<223> OTHER INFORMATION: Synthetic oligonucleotide primer

<400> SEQUENCE: 8
cgagctagcc atccaggtaa aacaaacaaa aacggatct                        39

<210> SEQ ID NO 9
<211> LENGTH: 34
<212> TYPE: DNA
<213> ORGANISM: Artificial Sequence
<220> FEATURE:
<223> OTHER INFORMATION: Synthetic oligonucleotide primer

<400> SEQUENCE: 9
attccatgga tcaggctgca taggacaaaa caag                             34

<210> SEQ ID NO 10
<211> LENGTH: 33
<212> TYPE: DNA
<213> ORGANISM: Artificial Sequence
<220> FEATURE:
<223> OTHER INFORMATION: Synthetic oligonucleotide primer

<400> SEQUENCE: 10
tagagagctc cagggttctt gcctggtgcc ttg                              33

<210> SEQ ID NO 11
<211> LENGTH: 33
<212> TYPE: DNA
<213> ORGANISM: Artificial Sequence
<220> FEATURE:
<223> OTHER INFORMATION: Synthetic oligonucleotide primer

<400> SEQUENCE: 11
acttctagat ggtgttttct gttacagagc aac                              33
```

TUBULIN REGULATORY ELEMENTS FOR USE IN PLANTS

This application is a division of U.S. application Ser. No. 10/925,392, filed Aug. 25, 2004, now U.S. Pat. No. 7,511,130 which claims the benefit of U.S. provisional patent application No. 60/497,523 filed Aug. 25, 2003, each of the disclosures of which are incorporated herein by reference in their entirety.

INCORPORATION OF SEQUENCE LISTING

Two copies of the sequence listing (Seq. Listing Copy 1 and Seq. Listing Copy 2) and a computer-readable form of the sequence listing, all on CD-ROMs, each containing the file named 53419-B ST25.txt, which is 10,240 bytes (measured in MS-DOS) and was created on Aug. 18, 2004, are hereby incorporated by reference.

FIELD OF THE INVENTION

The invention relates to the field of plant molecular biology and plant genetic engineering and polynucleotide molecules useful for the expression of transgenes in plants.

BACKGROUND

One of the goals of plant genetic engineering is to produce plants with agronomically desirable characteristics or traits. The proper expression of a desirable transgene in a transgenic plant is one way to achieve this goal. Regulatory elements such as promoters, leaders, and introns are non-coding polynucleotide molecules which play an integral part in the overall expression of genes in living cells. Isolated regulatory elements that function in plants are therefore useful for modifying plant phenotypes through the methods of genetic engineering.

Many regulatory elements are available and are useful for providing good overall expression of a transgene. For example, constitutive promoters such as P-FMV, the promoter from the 35S transcript of the Figwort mosaic virus (U.S. Pat. No. 6,051,753); P-CaMV 35S, the promoter from the 35S RNA transcript of the Cauliflower mosaic virus (U.S. Pat. No. 5,530,196); P-Rice Actin 1, the promoter from the actin 1 gene of Oryza sativa (U.S. Pat. No. 5,641,876); and P-NOS, the promoter from the nopaline synthase gene of Agrobacterium tumefaciens are known to provide some level of gene expression in most or all of the tissues of a plant during most or all of the plant's lifespan. While previous work has provided a number of regulatory elements useful to affect gene expression in transgenic plants, there is still a great need for novel regulatory elements with beneficial expression characteristics. Many previously identified regulatory elements fail to provide the patterns or levels of expression required to fully realize the benefits of expression of selected genes in transgenic crop plants.

Spatial organization within the eukaryotic cell and directed movements of the cell contents are mediated by the cytoskeleton, a network of filamentous protein polymers that permeates the cytosol. Tubulin is one of the three major families of proteins making up the cytoskeleton. Members of this multi-gene family have been reported in almost all eukaryotic species including yeast, humans, mouse, Drosophila, tobacco, maize, rice, soybean, potato and Arbabidopsis. There are two types of tubulin proteins in higher eukaryotes, α- and β-tubulin. Plant α- and β-tubulins are encoded by two gene families, each constituted by a number of different isotypes.

We hypothesized that a promoter from an α-tubulin gene might have a constitutive expression pattern and that the promoter and regulatory elements could be useful to direct expression of a transgene such as a glyphosate resistant 5-enolpyruvylshikimate-3-phosphate synthase (EPSPS) transgene to produce a glyphosate tolerant plant. The efficient production of glyphosate tolerant plants requires the use of a promoter and regulatory elements capable of directing transgene expression in all tissues including the most sensitive reproductive organs such as anthers and meristem tissues. The present invention thus provides such promoters and regulatory elements isolated from an α-tubulin gene of Oryza sativa.

SUMMARY

In one embodiment the invention provides polynucleotide molecules isolated from Oryza sativa useful for modulating transgene expression in plants. In another embodiment the invention provides expression constructs containing the polynucleotide molecules useful for modulating transgene expression in plants. In another embodiment the invention provides transgenic plants and seeds containing the polynucleotide molecules useful for modulating transgene expression in plants.

DETAILED DESCRIPTION

Figure 1:
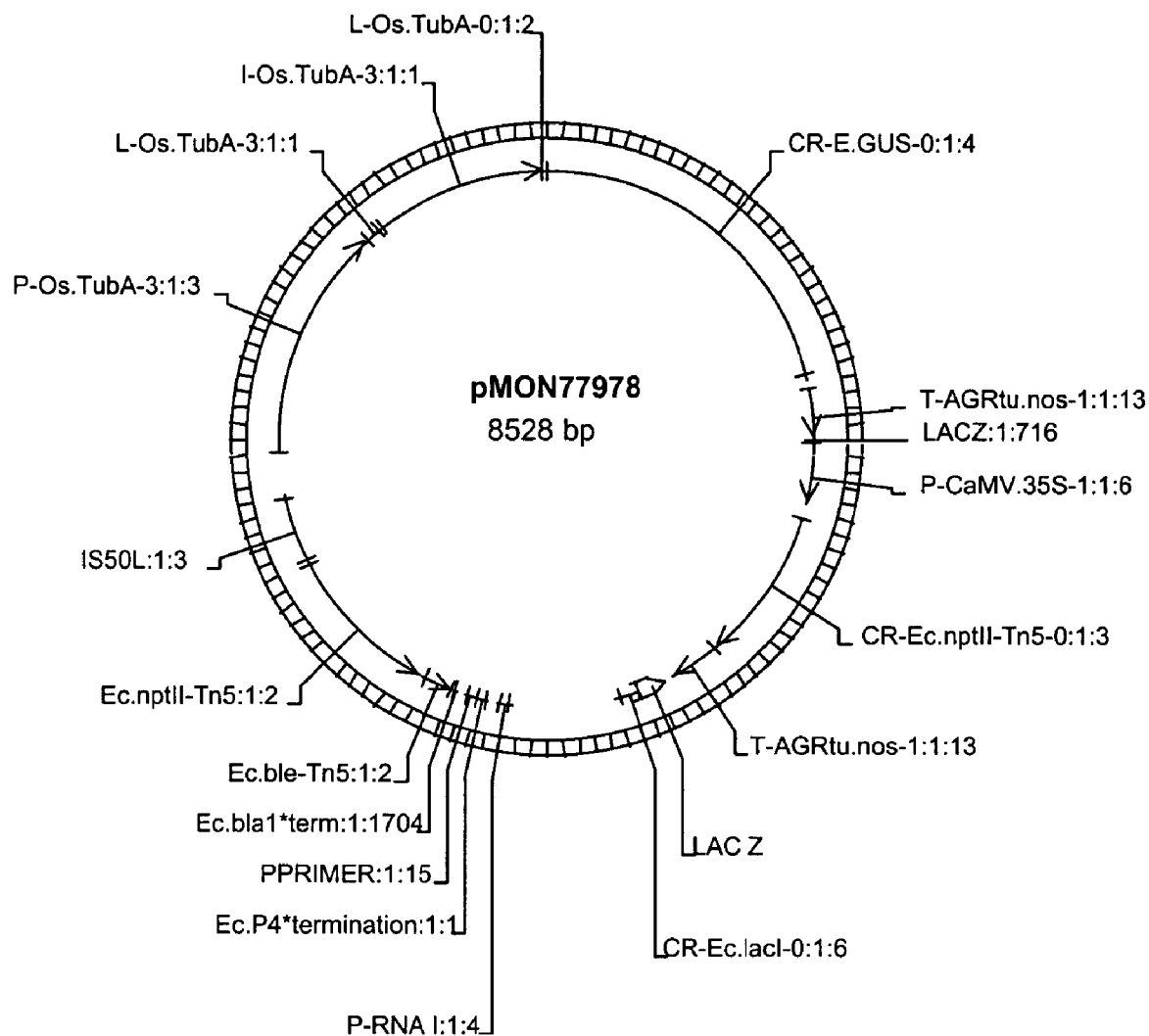
FIG. 1: pMON77978 plasmid map. Genetic elements and their relative position are shown. P=promoter; I=Intron; L=5' UTR; CR=coding region; T=3' region plus downstream sequence; nptII=kanamycin resistance gene, for plant and microbial selection.

The following definitions and methods are provided to better define the present invention and to guide those of ordinary skill in the art in the practice of the present invention. Unless otherwise noted, terms are to be understood according to conventional usage by those of ordinary skill in the relevant art.

The invention disclosed herein provides polynucleotide molecules having gene regulatory activity from Oryza sativa. The design, construction, and use of these polynucleotide molecules are one object of this invention. The polynucleotide sequences of these polynucleotide molecules are provided as SEQ ID NO: 1-5. These polynucleotide molecules are capable of affecting the transcription of operably linked transcribable polynucleotide molecules in both vegetative and reproductive tissues of plants and therefore can selectively regulate expression of transgenes in these tissues.

As used herein, the term "polynucleotide molecule" refers to the single- or double-stranded DNA or RNA of genomic or synthetic origin, i.e., a polymer of deoxyribonucleotide or ribonucleotide bases, respectively, read from the 5' (upstream) end to the 3' (downstream) end.

As used herein, the term "polynucleotide sequence" refers to the sequence of a polynucleotide molecule. The nomenclature for DNA bases as set forth at 37 CFR §1.822 is used.

As used herein, the term "gene regulatory activity" refers to a polynucleotide molecule capable of affecting transcription or translation of an operably linked transcribable polynucleotide molecule. An isolated polynucleotide molecule having gene regulatory activity may provide temporal or spatial expression or modulate levels and rates of expression of the operably linked transcribable polynucleotide molecule. An isolated polynucleotide molecule having gene regulatory activity may comprise a promoter, intron, leader, or 3' transcriptional termination region.

As used herein, the term "promoter" refers to a polynucleotide molecule that is involved in recognition and binding of RNA polymerase II and other proteins (trans-acting transcription factors) to initiate transcription. A "plant promoter" is a native or non-native promoter that is functional in plant cells. A plant promoter can be used as a 5' regulatory element for modulating expression of an operably linked gene or genes. Plant promoters may be defined by their temporal, spatial, or developmental expression pattern.

A promoter comprises subfragments that have promoter activity. Subfragments may comprise enhancer domains and may be useful for constructing chimeric promoters. Subfragments of SEQ ID NO: 1 comprise at least about 75, 85, 90, 95, 110, 125, 250, 400, 750, 1000, 1300, 1500, 1800, and 2000 contiguous nucleotides of the polynucleotide sequence of SEQ ID NO: 1, up to the full 2190 nucleotides of SEQ ID NO: 1. Subfragments of SEQ ID NO: 2 comprise at least about 95, 110, 125, 250, 400, 750, 1000, 1300, 1500, and 1800 contiguous nucleotides of the polynucleotide sequence of SEQ ID NO: 2, up to the full 1260 nucleotides of SEQ ID NO: 2.

As used herein, the term "enhancer domain" refers to a cis-acting transcriptional regulatory element, a.k.a. cis-element, which confers an aspect of the overall control of gene expression. An enhancer domain may function to bind transcription factors, trans-acting protein factors that regulate transcription. Some enhancer domains bind more than one transcription factor, and transcription factors may interact with different affinities with more than one enhancer domain. Enhancer domains can be identified by a number of techniques, including deletion analysis, i.e., deleting one or more nucleotides from the 5' end or internal to a promoter; DNA binding protein analysis using DNase I footprinting, methylation interference, electrophoresis mobility-shift assays, in vivo genomic footprinting by ligation-mediated PCR, and other conventional assays; or by DNA sequence similarity analysis with known cis-element motifs by conventional DNA sequence comparison methods. The fine structure of an enhancer domain can be further studied by mutagenesis (or substitution) of one or more nucleotides or by other conventional methods. Enhancer domains can be obtained by chemical synthesis or by isolation from promoters that include such elements, and they can be synthesized with additional flanking nucleotides that contain useful restriction enzyme sites to facilitate subsequence manipulation. Thus, the design, construction, and use of enhancer domains according to the methods disclosed herein for modulating the expression of operably linked polynucleotide molecules are encompassed by the present invention.

As used herein, the term "chimeric" refers to the product of the fusion of portions of two or more different polynucleotide molecules. As used herein, the term "chimeric promoter" refers to a promoter produced through the manipulation of known promoters or other polynucleotide molecules. Such chimeric promoters may combine enhancer domains that can confer or modulate gene expression from one or more promoters, for example, by fusing a heterologous enhancer domain from a first promoter to a second promoter with its own partial or complete regulatory elements. Thus, the design, construction, and use of chimeric promoters according to the methods disclosed herein for modulating the expression of operably linked polynucleotide molecules are encompassed by the present invention.

As used herein, the term "percent sequence identity" refers to the percentage of identical nucleotides in a linear polynucleotide sequence of a reference polynucleotide molecule (or its complementary strand) as compared to a test polynucleotide molecule (or its complementary strand) when the two sequences are optimally aligned (with appropriate nucleotide insertions, deletions, or gaps totaling less than 20 percent of the reference sequence over the window of comparison). Optimal alignment of sequences for aligning a comparison window are well known to those skilled in the art and may be conducted by tools such as the local homology algorithm of Smith and Waterman, the homology alignment algorithm of Needleman and Wunsch, the search for similarity method of Pearson and Lipman, and preferably by computerized implementations of these algorithms such as GAP, BESTFIT, FASTA, and TFASTA available as part of the GCG® Wisconsin Package® (Accelrys Inc., Burlington, Mass.). An "identity fraction" for aligned segments of a test sequence and a reference sequence is the number of identical components which are shared by the two aligned sequences divided by the total number of components in the reference sequence segment, i.e., the entire reference sequence or a smaller defined part of the reference sequence. Percent sequence identity is represented as the identity fraction multiplied by 100. The comparison of one or more polynucleotide sequences may be to a full-length polynucleotide sequence or a portion thereof, or to a longer polynucleotide sequence.

As used herein, the term "substantial percent sequence identity" refers to a percent sequence identity of at least about 70% sequence identity, at least about 80% sequence identity, at least about 90% sequence identity, or even greater sequence identity, such as about 98% or about 99% sequence identity. Thus, one embodiment of the invention is a polynucleotide molecule that has at least about 70% sequence identity, at least about 80% sequence identity, at least about 90% sequence identity, or even greater sequence identity, such as about 98% or about 99% sequence identity with a polynucleotide sequence described herein. Polynucleotide molecules that are capable of regulating transcription of operably linked transcribable polynucleotide molecules and have a substantial percent sequence identity to the polynucleotide sequences of the polynucleotide molecules provided herein are encompassed within the scope of this invention.

Promoter Isolation and Modification Methods

Any number of methods well known to those skilled in the art can be used to isolate fragments of a promoter disclosed herein. For example, PCR (polymerase chain reaction) technology can be used to amplify flanking regions from a genomic library of a plant using publicly available sequence information. A number of methods are known to those of skill in the art to amplify unknown polynucleotide molecules adjacent to a core region of known polynucleotide sequence. Methods include but are not limited to inverse PCR (IPCR), vectorette PCR, Y-shaped PCR, and genome walking approaches. Polynucleotide fragments can also be obtained by other techniques such as by directly synthesizing the fragment by chemical means, as is commonly practiced by using an automated oligonucleotide synthesizer. For the present invention, the polynucleotide molecules were isolated from genomic DNA by designing PCR primers based on available sequence information.

Novel chimeric promoters can be designed or engineered by a number of methods. For example, a chimeric promoter may be produced by fusing an enhancer domain from a first promoter to a second promoter. The resultant chimeric promoter may have novel expression properties relative to the first or second promoters. Novel chimeric promoters can be constructed such that the enhancer domain from a first promoter is fused at the 5' end, at the 3' end, or at any position internal to the second promoter. The location of the enhancer domain fusion relative to the second promoter may cause the resultant chimeric promoter to have novel expression properties relative to a fusion made at a different location.

Those of skill in the art are familiar with the standard resource materials that describe specific conditions and procedures for the construction, manipulation, and isolation of macromolecules (e.g., polynucleotide molecules, plasmids, etc.), as well as the generation of recombinant organisms and the screening and isolation of polynucleotide molecules.

Constructs

As used herein, the term "construct" refers to any recombinant polynucleotide molecule such as a plasmid, cosmid, virus, autonomously replicating polynucleotide molecule, phage, or linear or circular single-stranded or double-stranded DNA or RNA polynucleotide molecule, derived from any source, capable of genomic integration or autonomous replication, comprising a polynucleotide molecule where one or more polynucleotide molecule has been operably linked.

As used herein, the term "operably linked" refers to a first polynucleotide molecule, such as a promoter, connected with a second transcribable polynucleotide molecule, such as a gene of interest, where the polynucleotide molecules are so arranged that the first polynucleotide molecule affects the function of the second polynucleotide molecule. The two polynucleotide molecules may be part of a single contiguous polynucleotide molecule and may be adjacent. For example, a promoter is operably linked to a gene of interest if the promoter regulates or mediates transcription of the gene of interest in a cell.

As used herein, the term "transcribable polynucleotide molecule" refers to any polynucleotide molecule capable of being transcribed into a RNA molecule. Methods are known for introducing constructs into a cell in such a manner that the transcribable polynucleotide molecule is transcribed into a functional mRNA molecule that is translated and therefore expressed as a protein product. Constructs may also be constructed to be capable of expressing antisense RNA molecules, in order to inhibit translation of a specific RNA molecule of interest. For the practice of the present invention, conventional compositions and methods for preparing and using constructs and host cells are well known to one skilled in the art, see for example, *Molecular Cloning: A Laboratory Manual*, 3$^{rd}$ edition Volumes 1, 2, and 3 (2000) J. F. Sambrook, D. W. Russell, and N. Irwin, Cold Spring Harbor Laboratory Press.

Constructs of the present invention would typically contain a promoter operably linked to a transcribable polynucleotide molecule operably linked to a 3' transcription termination polynucleotide molecule. In addition, constructs may include but are not limited to additional regulatory polynucleotide molecules from the 3'-untranslated region (3' UTR) of plant genes (e.g., a 3' UTR to increase mRNA stability of the mRNA, such as the PI-II termination region of potato or the octopine or nopaline synthase 3' termination regions). Constructs may include but are not limited to the 5' untranslated regions (5' UTR) of an mRNA polynucleotide molecule which can play an important role in translation initiation and can also be a genetic component in a plant expression construct. For example, non-translated 5' leader polynucleotide molecules derived from heat shock protein genes have been demonstrated to enhance gene expression in plants (see for example, U.S. Pat. Nos. 5,659,122 and 5,362,865, all of which are hereby incorporated by reference). These additional upstream and downstream regulatory polynucleotide molecules may be derived from a source that is native or heterologous with respect to the other elements present on the promoter construct.

Thus, one embodiment of the invention is a promoter such as provided in SEQ ID NO: 1-2, operably linked to a transcribable polynucleotide molecule so as to direct transcription of said transcribable polynucleotide molecule at a desired level or in a desired tissue or developmental pattern upon introduction of said construct into a plant cell. In some cases, the transcribable polynucleotide molecule comprises a protein-coding region of a gene, and the promoter provides for transcription of a functional mRNA molecule that is translated and expressed as a protein product. Constructs may also be constructed for transcription of antisense RNA molecules or other similar inhibitory RNA in order to inhibit expression of a specific RNA molecule of interest in a target host cell.

Exemplary transcribable polynucleotide molecules for incorporation into constructs of the present invention include, for example, polynucleotide molecules or genes from a species other than the target gene species, or even genes that originate with or are present in the same species, but are incorporated into recipient cells by genetic engineering methods rather than classical reproduction or breeding techniques. Exogenous gene or genetic element is intended to refer to any gene or polynucleotide molecule that is introduced into a recipient cell. The type of polynucleotide molecule included in the exogenous polynucleotide molecule can include a polynucleotide molecule that is already present in the plant cell, a polynucleotide molecule from another plant, a polynucleotide molecule from a different organism, or a polynucleotide molecule generated externally, such as a polynucleotide molecule containing an antisense message of a gene, or a polynucleotide molecule encoding an artificial or modified version of a gene.

The promoters of the present invention can be incorporated into a construct using marker genes as described and tested in transient analyses that provide an indication of gene expression in stable plant systems. As used herein the term "marker gene" refers to any transcribable polynucleotide molecule whose expression can be screened for or scored in some way. Methods of testing for marker gene expression in transient assays are known to those of skill in the art. Transient expression of marker genes has been reported using a variety of plants, tissues, and DNA delivery systems. For example, types of transient analyses can include but are not limited to direct gene delivery via electroporation or particle bombardment of tissues in any transient plant assay using any plant species of interest. Such transient systems would include but are not limited to electroporation of protoplasts from a variety of tissue sources or particle bombardment of specific tissues of interest. The present invention encompasses the use of any transient expression system to evaluate promoters or promoter fragments operably linked to any transcribable polynucleotide molecules, including but not limited to selected reporter genes, marker genes, or genes of agronomic interest. Examples of plant tissues envisioned to test in transients via an appropriate delivery system would include but are not limited to leaf base tissues, callus, cotyledons, roots, endosperm, embryos, floral tissue, pollen, and epidermal tissue.

Any scorable or screenable marker gene can be used in a transient assay. Exemplary marker genes for transient analyses of the promoters or promoter fragments of the present invention include a GUS gene (U.S. Pat. No. 5,599,670, hereby incorporated by reference) or a GFP gene (U.S. Pat. Nos. 5,491,084 and 6,146,826, both of which are hereby incorporated by reference). The constructs containing the promoters or promoter fragments operably linked to a marker gene are delivered to the tissues and the tissues are analyzed by the appropriate mechanism, depending on the marker. The quantitative or qualitative analyses are used as a tool to evaluate the potential expression profile of the promoters or promoter fragments when operatively linked to genes of agronomic interest in stable plants.

Thus, in one preferred embodiment, a polynucleotide molecule of the present invention as shown in SEQ ID NO: 1-5 is incorporated into a construct such that a promoter of the present invention is operably linked to a transcribable polynucleotide molecule that provides for a selectable, screenable, or scorable marker. Markers for use in the practice of the present invention include, but are not limited to transcribable polynucleotide molecules encoding β-glucuronidase (GUS), green fluorescent protein (GFP), luciferase (LUC), proteins that confer antibiotic resistance, or proteins that confer herbicide tolerance. Useful antibiotic resistance markers, including those genes encoding proteins conferring resistance to kanamycin (nptII), hygromycin B (aph IV), streptomycin or spectinomycin (aad, spec/strep) and gentamycin (aac3 and aacC4) are known in the art. Herbicides for which transgenic plant tolerance has been demonstrated and the method of the present invention can be applied, include but are not limited to: glyphosate, glufosinate, sulfonylureas, imidazolinones, bromoxynil, delapon, cyclohezanedione, protoporphyrionogen oxidase inhibitors, and isoxasflutole herbicides.

Polynucleotide molecules encoding proteins involved in herbicide tolerance are known in the art, and include, but are not limited to a polynucleotide molecule encoding 5-enolpyruvylshikimate-3-phosphate synthase (EPSPS) described in U.S. Pat. Nos. 5,627,061, 5,633,435, and 6,040,497 and aroA described in U.S. Pat. No. 5,094,945 for glyphosate tolerance, all of which are hereby incorporated by reference; a polynucleotide molecule encoding bromoxynil nitrilase (Bxn) described in U.S. Pat. No. 4,810,648 for Bromoxynil tolerance, which is hereby incorporated by reference; a polynucleotide molecule encoding phytoene desaturase (crtI) described in Misawa et al, (1993) *Plant Journal* 4:833-840 and Misawa et al, (1994) *Plant Journal* 6:481-489 for norflurazon tolerance; a polynucleotide molecule encoding acetohydroxyacid synthase (AHAS, aka ALS) described in Sathasiivan et al. (1990) *Polynucleotides Research* 18:2188-2193 for tolerance to sulfonylurea herbicides; and the bar gene described in DeBlock, et al. (1987) *EMBO Journal* 6:2513-2519 for glufosinate and bialaphos tolerance.

In one embodiment of the invention, a polynucleotide molecule as shown in SEQ ID NO: 1-5 is incorporated into a construct such that a polynucleotide molecule of the present invention is operably linked to a transcribable polynucleotide molecule that is a gene of agronomic interest. As used herein, the term "gene of agronomic interest" refers to a transcribable polynucleotide molecule that includes but is not limited to a gene that provides a desirable characteristic associated with plant morphology, physiology, growth and development, yield, nutritional enhancement, disease or pest resistance, or environmental or chemical tolerance. The expression of a gene of agronomic interest is desirable in order to confer an agronomically important trait. A gene of agronomic interest that provides a beneficial agronomic trait to crop plants may be, for example, including, but not limited to genetic elements comprising herbicide resistance (U.S. Pat. Nos. 5,633,435 and 5,463,175), increased yield (U.S. Pat. No. 5,716,837), insect control (U.S. Pat. Nos. 6,063,597; 6,063,756; 6,093,695; 5,942,664; and 6,110,464), fungal disease resistance (U.S. Pat. Nos. 5,516,671; 5,773,696; 6,121,436; 6,316,407, and 6,506,962), virus resistance (U.S. Pat. Nos. 5,304,730 and 6,013,864), nematode resistance (U.S. Pat. No. 6,228,992), bacterial disease resistance (U.S. Pat. No. 5,516,671), starch production (U.S. Pat. Nos. 5,750,876 and 6,476,295), modified oils production (U.S. Pat. No. 6,444,876), high oil production (U.S. Pat. Nos. 5,608,149 and 6,476,295), modified fatty acid content (U.S. Pat. No. 6,537,750), high protein production (U.S. Pat. No. 6,380,466), fruit ripening (U.S. Pat. No. 5,512,466), enhanced animal and human nutrition (U.S. Pat. Nos. 5,985,605 and 6,171,640), biopolymers (U.S. Pat. No. 5,958,745 and U.S. Patent Publication No. US20030028917), environmental stress resistance (U.S. Pat. No. 6,072,103), pharmaceutical peptides (U.S. Pat. No. 6,080,560), improved processing traits (U.S. Pat. No. 6,476,295), improved digestibility (U.S. Pat. No. 6,531,648) low raffinose (U.S. Pat. No. 6,166,292), industrial enzyme production (U.S. Pat. No. 5,543,576), improved flavor (U.S. Pat. No. 6,011,199), nitrogen fixation (U.S. Pat. No. 5,229,114), hybrid seed production (U.S. Pat. No. 5,689,041), and biofuel production (U.S. Pat. No. 5,998,700). The genetic elements, methods, and transgenes described in the patents listed above are hereby incorporated by reference.

Alternatively, a transcribable polynucleotide molecule can effect the above mentioned phenotypes by encoding a RNA molecule that causes the targeted inhibition of expression of an endogenous gene, for example via antisense, inhibitory RNA (RNAi), or cosuppression-mediated mechanisms. The RNA could also be a catalytic RNA molecule (i.e., a ribozyme) engineered to cleave a desired endogenous mRNA product. Thus, any polynucleotide molecule that encodes a protein or mRNA that expresses a phenotype or morphology change of interest may be useful for the practice of the present invention.

The constructs of the present invention are generally double Ti plasmid border DNA constructs that have the right border (RB or AGRtu.RB) and left border (LB or AGRtu.LB) regions of the Ti plasmid isolated from *Agrobacterium tumefaciens* comprising a T-DNA, that along with transfer molecules provided by the *Agrobacterium* cells, permits the integration of the T-DNA into the genome of a plant cell. The constructs also contain the plasmid backbone DNA segments that provide replication function and antibiotic selection in bacterial cells, for example, an *Escherichia coli* origin of replication such as ori322, a broad host range origin of replication such as oriV or oriRi, and a coding region for a selectable marker such as Spec/Strp that encodes for Tn7 aminoglycoside adenyltransferase (aadA) conferring resistance to spectinomycin or streptomycin, or a gentamicin (Gm, Gent) selectable marker gene. For plant transformation, the host bacterial strain is often *Agrobacterium tumefaciens* ABI, C58, or LBA4404, however, other strains known to those skilled in the art of plant transformation can function in the present invention.

Transformed Plants and Plant Cells

As used herein, the term "transformed" refers to a cell, tissue, organ, or organism into which has been introduced a foreign polynucleotide molecule, such as a construct. The introduced polynucleotide molecule may be integrated into the genomic DNA of the recipient cell, tissue, organ, or organism such that the introduced polynucleotide molecule is inherited by subsequent progeny. A "transgenic" or "transformed" cell or organism also includes progeny of the cell or organism and progeny produced from a breeding program employing such a transgenic plant as a parent in a cross and exhibiting an altered phenotype resulting from the presence of a foreign polynucleotide molecule. A plant transformation construct containing a promoter of the present invention may be introduced into plants by any plant transformation method. Methods and materials for transforming plants by introducing a plant expression construct into a plant genome in the practice of this invention can include any of the well-known and demonstrated methods including electroporation as illustrated in U.S. Pat. No. 5,384,253; microprojectile bombardment as illustrated in U.S. Pat. Nos. 5,015,580; 5,550,318; 5,538,880; 6,160,208; 6,399,861; and 6,403,865; Agrobacterium-mediated transformation as illustrated in U.S. Pat. Nos. 5,824,877; 5,591,616; 5,981,840; and 6,384,301; and protoplast transformation as illustrated in U.S. Pat. No. 5,508,184, all of which are hereby incorporated by reference.

Methods for specifically transforming dicots are well known to those skilled in the art. Transformation and plant regeneration using these methods have been described for a number of crops including, but not limited to, cotton (*Gossypium hirsutum*), soybean (*Glycine max*), peanut (*Arachis hypogaea*), and members of the genus *Brassica*.

Methods for transforming monocots are well known to those skilled in the art. Transformation and plant regeneration using these methods have been described for a number of crops including, but not limited to, barley (*Hordeum vulgarae*); maize (*Zea mays*); oats (*Avena sativa*); orchard grass (*Dactylis glomerata*); rice (*Oryza sativa*, including indica and japonica varieties); sorghum (*Sorghum bicolor*); sugar cane (*Saccharum* sp); tall fescue (*Festuca arundinacea*); turfgrass species (e.g. species: *Agrostis stolonifera, Poa pratensis, Stenotaphrum secundatum*); wheat (*Triticum aestivum*), and alfalfa (*Medicago sativa*). It is apparent to those of skill in the art that a number of transformation methodologies can be used and modified for production of stable transgenic plants from any number of target crops of interest.

The transformed plants are analyzed for the presence of the genes of interest and the expression level and/or profile conferred by the promoters of the present invention. Those of skill in the art are aware of the numerous methods available for the analysis of transformed plants. For example, methods for plant analysis include, but are not limited to Southern blots or northern blots, PCR-based approaches, biochemical analyses, phenotypic screening methods, field evaluations, and immunodiagnostic assays.

The seeds of this invention can be harvested from fertile transgenic plants and be used to grow progeny generations of transformed plants of this invention including hybrid plant lines comprising the construct of this invention and expressing a gene of agronomic interest.

The present invention also provides for parts of the plants of the present invention. Plant parts, without limitation, include seed, endosperm, ovule and pollen. In a particularly preferred embodiment of the present invention, the plant part is a seed.

Still yet another aspect of the invention is a method of inhibiting weed growth in a field of transgenic crop plants comprising first planting the transgenic plants transformed with an expression cassette comprising an isolated polynucleotide molecule having gene regulatory activity and comprising a polynucleotide sequence selected from the group consisting of SEQ ID NO: 1-5 and operably linked to a DNA molecule encoding a glyphosate tolerance gene and then applying glyphosate to the field at an application rate that inhibits the growth of weeds, wherein the growth and yield of the transgenic crop plant is not substantially affected by the glyphosate application. The glyphosate application rate is the effective rate necessary to control weeds in a particular glyphosate tolerant crop; these rates may range from 8 ounces/acre to 256 ounces/acre, preferably 16 ounces/acre to 128 ounces/acre, and more preferably 32 ounces/acre to 96 ounces/acre. The glyphosate is applied at least once during the growth of the glyphosate tolerant crop and may be applied 2, 3, or 4 times during the growth of the crop or more as necessary to control weeds in the field.

The following examples are included to demonstrate preferred embodiments of the invention. It should be appreciated by those of skill in the art that the techniques disclosed in the examples that follow represent techniques discovered by the inventors to function well in the practice of the invention. However, those of skill in the art should, in light of the present disclosure, appreciate that many changes can be made in the specific embodiments that are disclosed and still obtain a like or similar result without departing from the spirit and scope of the invention, therefore all matter set forth or shown in the accompanying drawings is to be interpreted as illustrative and not in a limiting sense.

EXAMPLES

Example 1

Constitutive Gene Identification

Rice genes having a constitutive expression pattern were identified as the first step in isolating heterologous elements for use in the construction of transgene cassettes. Genes involved in basic cellular functions such as cytoskeleton formation are often constitutively expressed throughout the plant. These genes often exist in gene families, however, and while the overall expression of the family members may be constitutive throughout the plant, individual members may have more restricted, temporal, developmental, or organ/tissue/cell type specific expression patterns. With this understanding, specific gene families were focused on for the selection of individual candidate genes using data from gene expression studies.

The 5' untranslated region (UTR) sequences of members of selected multi-gene families (including tubulin, actin, histone, etc.) were identified using rice genomic sequence. Primers were designed to anneal to the 5' UTR sequences and PCR was performed using standard methods. The subsequent polynucleotide molecule products were arrayed on nylon filters for mRNA expression analysis. The filters were then probed with cDNA molecules derived from rice mRNA pools from root, leaf, grain, anther, ovary, or glume tissue. The experiment was repeated twice and results were used to analyze the expression of the selected genes. From analyzing the expression data, twenty genes were chosen for further analysis using real time PCR with 3' UTR specific primers. The primers were used in conjunction with the SYBR Green kit (Perkin Elmer Inc., Wellesley, Mass.) using a TAQMAN machine (thermocycler, Applied Biosystems, Foster City, Calif.) and standard protocols supplied by the manufacturer to amplify sequences out of leaf, root, anther, gynoecium, or apex cDNA. Results were then compared to the level of expression for the rice actin 1 gene, whose promoter and first intron are known to provide high glyphosate tolerance when operably linked to a glyphosate resistant EPSPS gene. An α-tubulin gene, designated Os-TubA-3, was shown to be expressed in rice in all tissues at levels higher than the ract1 gene.

The generally constitutive expression pattern of the Os-TubA-3 gene was further confirmed when a BLASTN analysis was performed using its 3' UTR sequence as a query of rice EST libraries prepared from various rice organs at various developmental stages (see Table 1). Results were again compared to the level of expression for the rice actin 1 gene. A particularly desirable expression feature of the TubA-3 gene was EST representation in developing floral structures, including anthers. A BLASTN search using the Os-TubA-3 3' UTR sequence was done to identify a rice BAC which contained a complete genomic copy of the Os-TubA-3 gene including the promoter region.

TABLE 1

Occurrence of respective 3' UTR sequences in rice EST libraries.

| Library | Total number of 5' and 3' reads | Rice actin 1 occurrences | Os-TubA-3 occurrences |
| --- | --- | --- | --- |
| panicle, cracking - ¾ open floret | 20,227 | 7 | >16 |
| developing panicle | 7,909 | 5 | >16 |
| late anther | 5,956 | 14 | 4 |
| developing seed | 7,453 | 1 | 8 |
| dry seed | 9,362 | 0 | 0 |
| germ. seed | 9,743 | 0 | 1 |
| vegetative apex | 7,672 | 2 | >16 |
| leaf, 3-5 leaf | 10,040 | 0 | 1 |
| leaf, 3-4 tiller | 9,209 | 1 | 0 |
| leaf, elong-boot | 7,897 | 1 | 3 |
| root, 3-5 leaf | 10,524 | 2 | 4 |
| root, 3-4 tiller | 10,624 | 1 | 9 |
| root, third tiller - milk | 7,481 | 1 | 3 |

Example 2

Constructs

The Os-TubA-3 promoter was isolated from the upstream genomic region of the Os-TubA-3 gene for incorporation into an expression cassette and subsequent characterization in transgenic plants. Oligonucleotides OsTUBA136-1 and OsTUBA136-2 (provided as SEQ ID NO: 6 and SEQ ID NO: 7, respectively) were designed to amplify the 5' region (promoter and 5' UTR). The upstream promoter region of the Os-TubA-3 gene was amplified starting immediately upstream of the translation initiation codon and ending approximately 1.2 kb immediately upstream of the start of transcription initiation site (inferred by looking at the longest 5'UTR present for the Os-TubA-3 gene in the EST collection). The promoter sequence is provided as SEQ ID NO: 2. The leader sequence is provided as SEQ ID NO: 5. The first intron of the Os-TubA-3 gene (which lies downstream of the start of translation) was amplified with oligonucleotides OsTUBA136-3 and OsTubA136-4 (provided as SEQ ID NO: 8 and SEQ ID NO: 9, respectively). The intron sequence is provided as SEQ ID NO: 4. The intron was then removed from its native context and placed within the 5'UTR immediately upstream of the translation initiation codon to produce a chimeric Os-TubA-3 promoter. The chimeric promoter sequence is provided as SEQ ID NO: 1.

Constructs for in planta Os-TubA-3 promoter characterization for expression of an operably linked transgene were then created. The promoter was ligated into a plant expression construct such that the promoter was operably linked to the transgene of interest.

Figure 2:
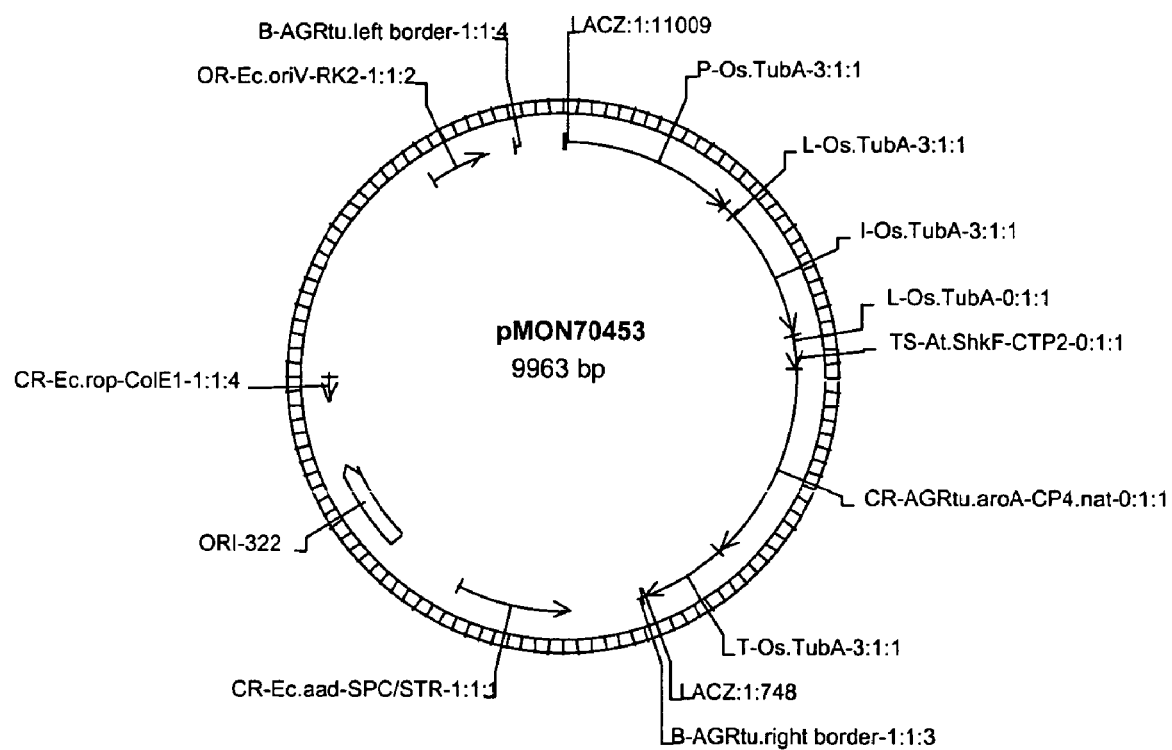
FIG. 2: pMON70453 plasmid map. Genetic elements and their relative position are shown. P=promoter; I=Intron; L=5' UTR; TS=transit peptide sequence; CR=coding region; T=3' region plus downstream sequence; CP4=glyphosate resistance gene for plant selection; SPC/STR=aad for microbial selection; left and right T-DNA borders are shown.

The Os-TubA-3 3' region (500-600 bp of sequence immediately downstream of the translation termination codon which includes the 3' UTR plus adjacent downstream sequence) was also amplified using oligonucleotides OsTUBA136-5 and OsTUBA136-6 (provided as SEQ ID NO: 10 and SEQ ID NO: 11). The 3' region sequence is provided as SEQ ID NO: 3. The 3' region was used in constructing the plant transformation vector in order to provide further element diversity over existing constructs and to capture any regulatory capacity (transcriptional or at the level of mRNA stability) present within the sequence. The Os-TubA-3 3' region was ligated onto the 3' end of the transgene of interest. For GUS activity characterization the plant transformation vector pMON77978 as shown in FIG. 1 contains the GUS reporter gene as the transgene of interest. For glyphosate tolerance characterization the plant transformation vector pMON70453 as shown in FIG. 2 contains the CTP2/CP4 EPSPS gene as the transgene of interest.

Example 3

Promoter Characterization in Transient Systems

The plant expression vector pMON77978 was used to transform maize callus using particle bombardment for in planta promoter characterization. The GUS activity was then analyzed quantitatively. Results are shown in Table 2. The Os-TubA-3 promoter was shown to have a desirable level of expression in this transient system.

TABLE 2

Quantitative Analysis of GUS activity in maize callus.

| Construct | GUS activity (pmoles/μg protein/hour) |
| --- | --- |
| Os-TubA-3 (pMON77978) | 17.51 ± 2.16 |
| E35S (pMON77952) | 33.53 ± 11.28 |
| Blank Control promoterless GUS vector (pMON77951) | 1.67 ± 0.502 |

Example 4

Promoter Characterization in Transgenic Plants

The plant expression vector pMON70453 was used to transform corn using an *Agrobacterium* mediated transformation method. For example, a disarmed *Agrobacterium* strain C58 harboring a binary DNA construct of the present invention is used. The DNA construct is transferred into *Agrobacterium* by a triparental mating method (Ditta et al., Proc. Natl. Acad. Sci. 77:7347-7351, 1980). Liquid cultures of *Agrobacterium* are initiated from glycerol stocks or from a freshly streaked plate and grown overnight at 26° C.-28° C. with shaking (approximately 150 rpm) to mid-log growth phase in liquid LB medium, pH 7.0 containing the appropriate antibiotics. The *Agrobacterium* cells are resuspended in the inoculation medium (liquid CM4C) and the density is adjusted to $OD_{660}$ of 1. Freshly isolated Type II immature HiIIxLH198 and HiII corn embryos are inoculated with *Agrobacterium* containing a construct and co-cultured several days in the dark at 23° C. The embryos are then transferred to delay media and incubated at 28° C. for several or more days. All subsequent cultures are kept at this temperature. The embryos are transferred to a first selection medium containing carbenicillin 500/0.5 mM glyphosate. Two weeks later, surviving tissue are transferred to a second selection medium containing carbenicillin 500/1.0 mM glyphosate. Subculture surviving callus every 2 weeks until events can be identified. This may take about 3 subcultures on 1.0 mM glyphosate. Once events are identified, bulk up the tissue to regenerate. The plantlets (events) are transferred to MSOD media in culture vessel and kept for two weeks. The transformation efficiency is determined by dividing the number of events produced by the number of embryos inoculated. Then the plants with roots are transferred into soil. Those skilled in the art of monocot transformation methods can modify this method to provide substantially identical transgenic monocot plants containing the DNA compositions of the present invention, or use other methods, such as particle gun, that are known to provide transgenic monocot plants.

Approximately 25 events per construct were generated. Events were selected on glyphosate containing medium, transferred to soil, and then moved to the greenhouse. In the greenhouse, plants were sprayed with glyphosate (0.84 kg glyphosate acid equivalents·ha$^{-1}$) using the ROUNDUP ULTRA formulation at approximately V4 leaf stage. Plants that survived without injury (<10% chlorosis and malformation) were kept and transferred to large pots. At approximately V8 stage, a second glyphosate application was made as before. This second spray was to evaluate male reproductive tolerance. Events from the new constructs were scored for male fertility upon maturation of the tassels. The Male Fertility Rating (MFR) is scored on a range where MFR=1 is completely sterility (for tassels lacking developed florets) and MFR=5 is full pollen shed (for fully developed anthers with pollen shed); MFR=4-5 is considered commercially viable. A combination of Taqman and Southern analysis were used to evaluate the transgene copy number in the events going to the greenhouse. Southern analysis using the new elements also showed that these heterologous sequences do not exhibit cross hybridization to endogenous maize sequences—a significant quality for event characterization. These early evaluations are part of a process to select cassettes equivalent to P-Os.Act1/CP4. Important criteria for a successful construct include good transformation efficiency (number of events produced/# explants inoculated) and the ability to reproducibly provide vegetatively and reproductively tolerant transformants carrying a single copy of the transgene. A summary of the early transformation and greenhouse evaluations is shown in Table 3. Single copy events that passed greenhouse evaluations were advanced to field evaluations.

Field evaluations were done in Puerto Rico with F2 generation corn plants. Plants were treated with two applications of 3.36 kg glyphosate acid equivalents·ha$^{-1}$ in ROUNDUP ULTRAMAX formulation (4× above current field use rate). One treatment was done at V4 stage and a second treatment was done at V8 stage. The vegetative ratings for chlorosis (<10% chlorosis) and malformation (<10% malformation) were taken 10 days after treatment. Male fertility ratings (MFR) were taken at tassel maturity. For comparison, commercial event NK603 (pMON25496 containing P-Os.Act1/CP4 EPSPS::P-e35S/CP4 EPSPS) was evaluated. Results are shown in Table 4.

TABLE 4

Field Evaluation.

| Construct | Number of Events | Events that passed V8 malformation rating | Events that passed V8 chlorosis rating | Events that passed vegetative ratings and MFR = 4-5 |
|---|---|---|---|---|
| P-Os.Act1 + E35S NK603 | 1 | 1 | 1 | 1 |
| P-Os.TubA-3 pMON70453 | 7 | 6 | 6 | 6 |

CP4 EPSPS protein accumulation (μg/mg of total protein shown as mean±standard error) in various corn tissues was then measured for single copy events in hemi-zygous F1 plants that showed good field efficacy for glyphosate tolerance. For comparison, commercial event NK603 has approximately 21 ppm or approximately 1.4 μg CP4 EPSPS/mg total protein in V4 leaf lamina stage when grown under similar conditions. Results are shown in Table 5.

TABLE 3

Early transformation and greenhouse evaluations.

| Construct | Transformation Frequency | Number of Events | Single Copy | Single copy and vegetatively tolerant in R0 | Single copy, vegetatively tolerant and MFR = 4-5 in R0 |
|---|---|---|---|---|---|
| P-Os.Act1 pMON30167 | 5.1% | 24 | 33% | 21% | 21 |
| P-Os.TubA-3 pMON70453 | 5.2% | 49 | 53% | 37% | 33 |

TABLE 5

CP4 EPSPS accumulation in various corn tissues.

| Construct | Number of single copy events | V4 leaf lamina at V4 stage | V9-10 leaf lamina at V9-10 stage | Immature Tassel (5-10 cm) | Root tip (~1 cm) |
|---|---|---|---|---|---|
| P-Os.TubA-3 pMON70453 | 10 | 0.041 ± 0.005 | 0.070 ± 0.006 | 0.144 ± 0.014 | 0.095 ± 0.016 |

Having illustrated and described the principles of the present invention, it should be apparent to persons skilled in the art that the invention can be modified in arrangement and detail without departing from such principles. We claim all modifications that are within the spirit and scope of the appended claims. All publications and published patent documents cited in this specification are incorporated herein by reference to the same extent as if each individual publication or patent application is specifically and individually indicated to be incorporated by reference.

We claim:

1. A construct comprising a polynucleotide molecule having gene regulatory activity and having at least 98% sequence identity to SEQ ID NO:2; wherein the polynucleotide molecule having gene regulatory activity is operably linked to a heterologous transcribable polynucleotide molecule.

2. The construct according to claim 1, wherein said polynucleotide molecule comprising the polynucleotide sequence of SEQ ID NO:2.

3. The construct of claim 1, wherein said heterologous transcribable polynucleotide molecule is a marker.

4. The construct of claim 1, wherein said heterologous transcribable polynucleotide molecule is a sequence of agronomic interest.

5. The construct of claim 4, wherein said sequence of agronomic interest confers herbicide tolerance and is selected from the group consisting of sequences that encode phosphinothricin acetyltransferase, glyphosate resistant 5-enolpyruvylshikimate-3-phosphate synthase, hydroxyphenyl pyruvate dehydrogenase, dalapon dehalogenase, bromoxynil resistant nitrilase, anthranilate synthase, glyphosate oxidoreductase and glyphosate-N-acetyl transferase.

6. A transgenic plant stably transformed with the construct of claim 1.

7. The transgenic plant of claim 6, wherein said plant is a monocotyledonous plant selected from the group consisting of wheat, maize, rye, rice, oat, barley, turfgrass, sorghum, millet and sugarcane.

8. The transgenic plant of claim 6, wherein said plant is a dicotyledonous plant selected from the group consisting of tobacco, tomato, potato, soybean, cotton, canola, sunflower and alfalfa.

9. A seed of said transgenic plant of claim 6, wherein the seed comprises the construct.

10. A method of inhibiting weed growth in a field of transgenic glyphosate tolerant crop plants comprising:

i) planting transgenic plants transformed with the construct of claim 1, wherein the heterologous transcribable polynucleotide confers glyphosate tolerance when expressed in a plant, and ii) applying glyphosate to the field at an application rate that inhibits the growth of weeds, wherein the growth and yield of the transgenic crop plant is not substantially affected by the glyphosate application.

11. The method of claim 10, wherein said transcribable polynucleotide is selected from the group consisting of a polynucleotide encoding a glyphosate resistant 5-enolpyruvylshikimate-3-phosphate synthase, a glyphosate oxidoreductase, and a glyphosate-N-acetyl transferase.

12. The method of claim 10, wherein the transgenic plants are capable of tolerating an application rate up to 256 ounces/acre.

13. The method of claim 10, wherein the transgenic plants are capable of tolerating an application rate ranging from 8 ounces/acre to 128 ounces/acre.

14. The method of claim 10, wherein the transgenic plants are capable of tolerating an application rate ranging from 32 ounces/acre to 96 ounces/acre.

15. The method of claim 10, wherein the application of glyphosate is at least once during the growth of the crop.

16. The transgenic plant of claim 6, wherein said transcribable polynucleotide molecule is a marker.

17. The transgenic plant of claim 6, wherein said transcribable polynucleotide molecule is a sequence of agronomic interest.

18. The transgenic plant of claim 17, wherein said sequence of agronomic interest confers herbicide tolerance and is selected from the group consisting of sequences that encode phosphinothricin acetyltransferase, glyphosate resistant 5-enolpyruvylshikimate-3-phosphate synthase, hydroxyphenyl pyruvate dehydrogenase, dalapon dehalogenase, bromoxynil resistant nitrilase, anthranilate synthase, glyphosate oxidoreductase and glyphosate-N-acetyl transferase.

* * * * *

UNITED STATES PATENT AND TRADEMARK OFFICE
CERTIFICATE OF CORRECTION

PATENT NO.         : 7,838,654 B2                                    Page 1 of 1
APPLICATION NO.    : 12/389314
DATED              : November 23, 2010
INVENTOR(S)        : Heck et al.

It is certified that error appears in the above-identified patent and that said Letters Patent is hereby corrected as shown below:

In claim 2, column 23, line 8, delete "comprising" and insert --comprises--.

Signed and Sealed this
Nineteenth Day of July, 2011

David J. Kappos
*Director of the United States Patent and Trademark Office*